(12) United States Patent
Hartley et al.

(10) Patent No.: US 12,213,825 B2
(45) Date of Patent: Feb. 4, 2025

(54) AUGMENTED FLUOROSCOPY WITH DIGITAL SUBTRACTION IMAGING

(71) Applicant: The Board of Trustees of the Leland Stanford Junior University, Stanford, CA (US)

(72) Inventors: Bryan I. Hartley, Redwood City, CA (US); Harmeet Bedi, Palo Alto, CA (US); Rene Vargas-Voracek, Sunnyvale, CA (US); Norbert J. Pelc, Aptos, CA (US)

(73) Assignees: The Board of Trustees of the Leland Stanford Junior University, Stanford, CA (US); Pulmera, Inc., Redwood City, CA (US)

( * ) Notice: Subject to any disclaimer, the term of this patent is extended or adjusted under 35 U.S.C. 154(b) by 308 days.

(21) Appl. No.: 17/733,772

(22) Filed: Apr. 29, 2022

(65) Prior Publication Data

US 2022/0257206 A1    Aug. 18, 2022

Related U.S. Application Data

(63) Continuation-in-part of application No. 16/998,278, filed on Aug. 20, 2020, now Pat. No. 12,004,707.
(Continued)

(51) Int. Cl.
*A61B 6/00*    (2024.01)
*A61B 6/02*    (2006.01)
(Continued)

(52) U.S. Cl.
CPC .............. *A61B 6/487* (2013.01); *A61B 6/022* (2013.01); *A61B 6/0492* (2013.01);
(Continued)

(58) Field of Classification Search
CPC ....................................................... A61B 8/487
See application file for complete search history.

(56) References Cited

U.S. PATENT DOCUMENTS 6,484,049 B1 * 11/2002 Seeley .................. A61B 90/36
600/431
8,821,376 B2    9/2014 Tolkowsky
(Continued)

*Primary Examiner* — Joel F Brutus
(74) *Attorney, Agent, or Firm* — LUMEN PATENT FIRM

(57) ABSTRACT

A method of x-ray fluoroscopy images a region of interest at distinct first and second imaging projection angles using digital subtraction x-ray fluoroscopic imaging with a fiducial marker board positioned in a field of view containing the region of interest to produce first and second sets of images. Image segmentation information is determined to identify an anatomical feature in the region of interest imaged in the first set of images and the second set of images. The region of interest is then imaged using x-ray fluoroscopic imaging, again with the fiducial marker board positioned in a third field of view containing the region of interest, but without digital subtraction, to produce a third set of images. A virtual image of the anatomical feature is projected onto the third set of images, computed from the image segmentation information and from a predetermined geometric relationship of markers within the fiducial marker board.

6 Claims, 7 Drawing Sheets

Related U.S. Application Data which is a continuation of application No. PCT/US2019/027949, filed on Apr. 17, 2019.

(60) Provisional application No. 62/737,793, filed on Sep. 27, 2018, provisional application No. 62/659,032, filed on Apr. 17, 2018.

(51) Int. Cl.
  *A61B 6/04* (2006.01)
  *A61B 6/46* (2024.01)
  *A61B 6/50* (2024.01)
  *A61B 90/00* (2016.01)
  *G06T 5/50* (2006.01)

(52) U.S. Cl.
  CPC ............ *A61B 6/4441* (2013.01); *A61B 6/469* (2013.01); *A61B 6/481* (2013.01); *A61B 6/50* (2013.01); *A61B 6/5217* (2013.01); *A61B 6/5235* (2013.01); *A61B 90/39* (2016.02); *G06T 5/50* (2013.01); *A61B 2090/3966* (2016.02)

(56) References Cited

U.S. PATENT DOCUMENTS

| | | | |
|---|---|---|---|
| 2005/0182295 A1* | 8/2005 | Soper | A61B 1/2676 600/117 |
| 2014/0275777 A1* | 9/2014 | Gunday | A61B 17/320725 600/109 |
| 2016/0287223 A1* | 10/2016 | Hingston | A61B 8/12 |
| 2018/0035966 A1* | 2/2018 | Merlet | G06T 7/33 |
| 2019/0038365 A1 | 2/2019 | Soper | |
| 2020/0375448 A1 | 12/2020 | Hartley | |

* cited by examiner

AUGMENTED FLUOROSCOPY WITH DIGITAL SUBTRACTION IMAGING

CROSS-REFERENCE TO RELATED APPLICATIONS

This application claims priority from U.S. Provisional Patent Application 63/182,118 filed Apr. 30, 2021, which is incorporated herein by reference. This application is a continuation-in-part of U.S. patent application Ser. No. 16/998,278 filed Aug. 20, 2020, which is a continuation of International Patent Application PCT/US2019/027949 filed Apr. 17, 2019, which claims the benefit of priority to U.S. Provisional Patent Applications 62/659,032 filed Apr. 17, 2018 and 62/737,793 filed Sep. 27, 2018, each of which is incorporated herein by reference in its entirety.

STATEMENT OF FEDERALLY SPONSORED RESEARCH

This invention was made with Government support under contract CA243927 awarded by the National Institutes of Health. The Government has certain rights in the invention.

FIELD OF THE INVENTION

The present invention relates generally to medical imaging devices and methods. More specifically, it relates to techniques for fluoroscopy.

BACKGROUND OF THE INVENTION

Lung cancer is the leading cancer killer, killing more people than breast, prostate and colon cancers combined each year in the US. The key to improving survival is early diagnosis and treatment. Diagnosis is commonly performed by a bronchoscopic lung biopsy, where a bronchoscope is inserted into the lung and a catheter inserted through the bronchoscope is navigated through the airways to the nodule where a needle biopsy is performed. X-ray is often used to visualize the catheter and the needle during biopsy. One significant problem with this approach is that pulmonary nodules are often invisible on x-ray images, leaving the physician to use alternative navigation technologies such as electromagnetic navigation. One recent concept is to use air pressure inflation to visualize these nodules with digital subtraction imaging (US20200375448A1). Air inflation with digital subtraction imaging often leads to invisible nodules becoming visible, thus helping the physician to locate and navigate to the nodule for biopsy. However, one downside with this technique is that the nodule is only visible during the image acquisition where the lung tissue is being inflated under subtraction imaging. Once the subtraction imaging acquisition ends, the nodule is no longer visible. This leads to the physician performing multiple air inflation procedures during the procedure to maintain nodule visualization for navigation. These additional inflation/subtraction imaging acquisitions required during the procedure increases both time and radiation exposure.

SUMMARY OF THE INVENTION

Visualizing pulmonary nodules during lung biopsy is challenging using x-ray fluoroscopy. The inventors have previously developed a method to visualize nodules using air pressure to enhance the appearance of the nodule on x-ray. However, using this technique the nodule is only visible during the time when air pressure is being injected into the airway. We have now developed and herein disclose a method and system to visualize the pulmonary nodule continuously using augmented fluoroscopy.

This disclosure is related to navigation within the lungs via bronchoscopy to pulmonary nodules. It has applications in the biopsy and minimally invasive treatment of suspected early stage lung cancer. In one aspect, a navigation system is provided with catheter, air pressure pump and image processing unit. The invention provides a system and method. In one implementation, the system and method uses an x-ray fiducial marker board (e.g., thin board with metallic beads forming a grid) with air pressures to initially visualize a pulmonary nodule. Once the nodule is visualized, the x-ray C arm is rotated to an oblique angle and the air pressure maneuver is repeated once again until the nodule is visualized. Once the nodule is visualized and selected/segmented in both angles, the system (using computer processing) can then triangulate the nodule's location within any subsequent images that may be acquired without the use of air pressures. Basically, the initial nodule visualization plus the stationary marker grid allows the location of the nodule to be determined at many different angles with respect to the marker grid, allowing the physician to navigate to the target while simultaneously viewing the virtual nodule on the x-ray.

Advantages over existing products include the ability to locate a pulmonary nodule on x-ray during a procedure without having to perform a CT. This technology allows the user to visualize the nodule continuously during the procedure with a high degree of accuracy.

In one aspect the invention provides a method of x-ray fluoroscopy comprising: imaging a region of interest at a first imaging projection angle using digital subtraction x-ray fluoroscopic imaging with a fiducial marker board positioned in a first field of view containing the region of interest to produce a first set of images; is imaging the region of interest at a second imaging projection angle using digital subtraction x-ray fluoroscopic imaging with the fiducial marker board positioned in a second field of view containing the region of interest to produce a second set of images; determining image segmentation information to identify an anatomical feature in the region of interest imaged in the first set of images and the second set of images; imaging the region of interest using x-ray fluoroscopic imaging with the fiducial marker board positioned in a third field of view containing the region of interest to produce a third set of images; and projecting a virtual image of the anatomical feature onto the third set of images, where the virtual image is computed from the image segmentation information to identify the anatomical feature in the region of interest, from images of the fiducial marker board, and from a predetermined geometric relationship of markers within the fiducial marker board.

In some embodiments, the region of interest is a lung, the anatomical feature is a pulmonary nodule, imaging the region of interest at the first imaging projection angle using digital subtraction x-ray fluoroscopic imaging comprises performing bronchoscopy with air pressure inflation of the lung near the pulmonary nodule, and imaging the region of interest at the second imaging projection angle using digital subtraction x-ray fluoroscopic imaging comprises performing bronchoscopy with air pressure inflation of the lung near the pulmonary nodule.

In some embodiments, performing bronchoscopy with air pressure inflation of the lung near the pulmonary nodule is performed using a catheter with an expandable occluding device disposed at a distal end, air pumps, and air valves.

In some embodiments, performing bronchoscopy with air pressure inflation of the is lung near the pulmonary nodule comprises expanding an occluding device disposed at a distal end of a catheter to occlude an airway segment and inflating the airway segment.

In some embodiments, the fiducial marker board comprises multiple rows of radio-dense markers embedded within a board with a predetermined geometric arrangement.

In some embodiments, imaging the region of interest at the first imaging projection angle using digital subtraction x-ray fluoroscopic imaging is performed using a fluoroscopic x-ray C-arm device; imaging the region of interest at the second imaging projection angle using digital subtraction x-ray fluoroscopic imaging is performed using the fluoroscopic x-ray C-arm device; and the method further comprises rotating the fluoroscopic x-ray C-arm device between imaging the region of interest at the first imaging projection angle and imaging the region of interest at the second imaging projection angle.

In some embodiments, determining the image segmentation information is performed automatically using digital image processing.

DETAILED DESCRIPTION OF THE INVENTION

Described herein is a technique to maintain visualization of a nodule after an air inflation/subtraction series of images have been performed. A system and method is provided to improve the visualization of pulmonary structures on fluoroscopic x-ray to help guide physicians during pulmonary procedures. The technique builds on techniques for structure visualization in the lung (US20200375448A1) using air pressure. Specifically, this system uses air inflation of a pressure isolated segment of lung while using digital subtraction x-ray fluoroscopy to visualize structures such as pulmonary nodules which do not inflate. The inflated segment of lung becomes enhanced as the air fills the lung tissue while the pulmonary nodule does not enhance, leaving a shadow of the pulmonary nodule on the image. This occurs even if the nodule was not visible on x-ray previously. However, because the visibility of the nodule is dependent on subtraction imaging, the procedure described in US20200375448A1 must be repeated each time the physician wants to locate the nodule. Thus, there is a need in the art to allow for nodule visualization on x-ray images without having to repeat the inflation-subtraction imaging procedure.

Figure 1:
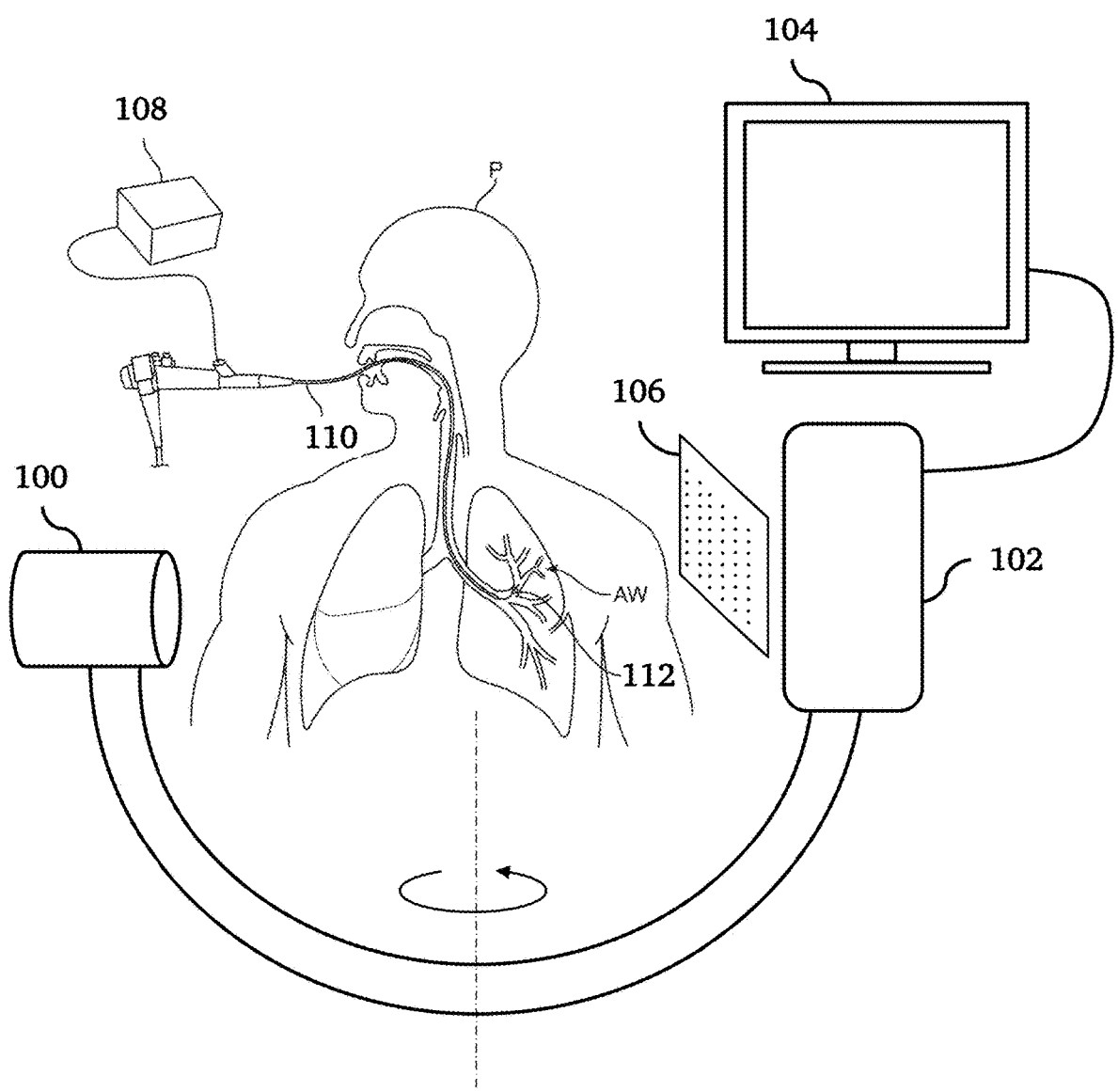
FIG. 1 is an illustration of an example system including x-ray C-arm, fiducial marker board with radio-dense beads, pressure controller, catheter with occluding device at the end, and computer processor, according to an embodiment of the invention.

FIG. 1 shows a system according to an embodiment of the invention comprised of an x-ray source 100, x-ray detector 102, air pressure controller device 108, fiducial marker board 106, catheter 110 with occluding device 112, and computer 104 with display and processor. The x-ray source/detector pair 100/102 can be a fluoroscopic x-ray C-arm device that can be positioned and rotated around a patient P. The detector 102 can be an image intensifier or a flat panel detector. The C-arm can be manually or mechanically rotated while acquiring x-ray images. The fiducial marker board 106 is fixed in a predetermined, stationary position and orientation relative to the patient/target. The fiducial marker board 106 is composed of an x-ray transparent board containing radio-dense beads.

The air pressure controller device 108 and catheter 110 with occluding device 112 at the distal end are described in further detail in US20200375448A1. Briefly, the air pressure controller device can be automatically or manually operated and can be composed of a system of pumps, valves, microcontrollers, syringes with pressure valves. The pressure controller device could inflate to a pressure range of 0-100 cmH20 with safety pressure release valves. The pressure controller could also be manually actuated and represent a syringe with pressure release valve with cracking pressure in a range of 20-400 cmH20. The catheter with an occluding device could be composed of a catheter with at least one lumen and which has an occluding device radially disposed at the distal extent. The occluding device could represent a balloon which could be expandable to occlude a segment of an airway for example. The catheter could represent a bronchoscope and have a flexible tip for steering within the lumen of a body such as the airways.

The fiducial marker board 106 is placed between the patient and the x-ray source/detector pair. The fiducial board may be composed of multiple rows of radio-dense or metallic markers embedded within the board with a known pattern and geometric relationship. The markers could be metallic beads or ball bearings embedded within a hard plastic that is radiolucent (e.g., resin or PVC). The beads could be arranged in a pattern with known distances between the markers. For example, the beads could be 1-10 mm in diameter and be spaced every 1-5 cm apart with a known spatial relationship between the beads. The fiducial board could be 1-30 mm thick.

Described herein is also a method to visualize the pulmonary structures e.g. pulmonary nodules without having to continuously repeat the air inflation maneuver. The method involves visualizing a structure such as a nodule with subtraction imaging with air inflation then rotating the projection angle of the x-ray source/detector to another projection angle and repeating the air inflation maneuver to visualize the structure at another projection with subtraction imaging. Next, the structure is segmented in each projection and the spatial location of the structure is determined relative to the fiducial marker board. Once the location of the structure is determined relative to the board, a virtual projection of the structure can be overlaid onto any subsequent live x-ray fluoroscopic images, even if the c-arm is rotating and no digital subtraction is performed, by continuously updating the location on the projection image relative to the fiducial marker board.

Figure 2:
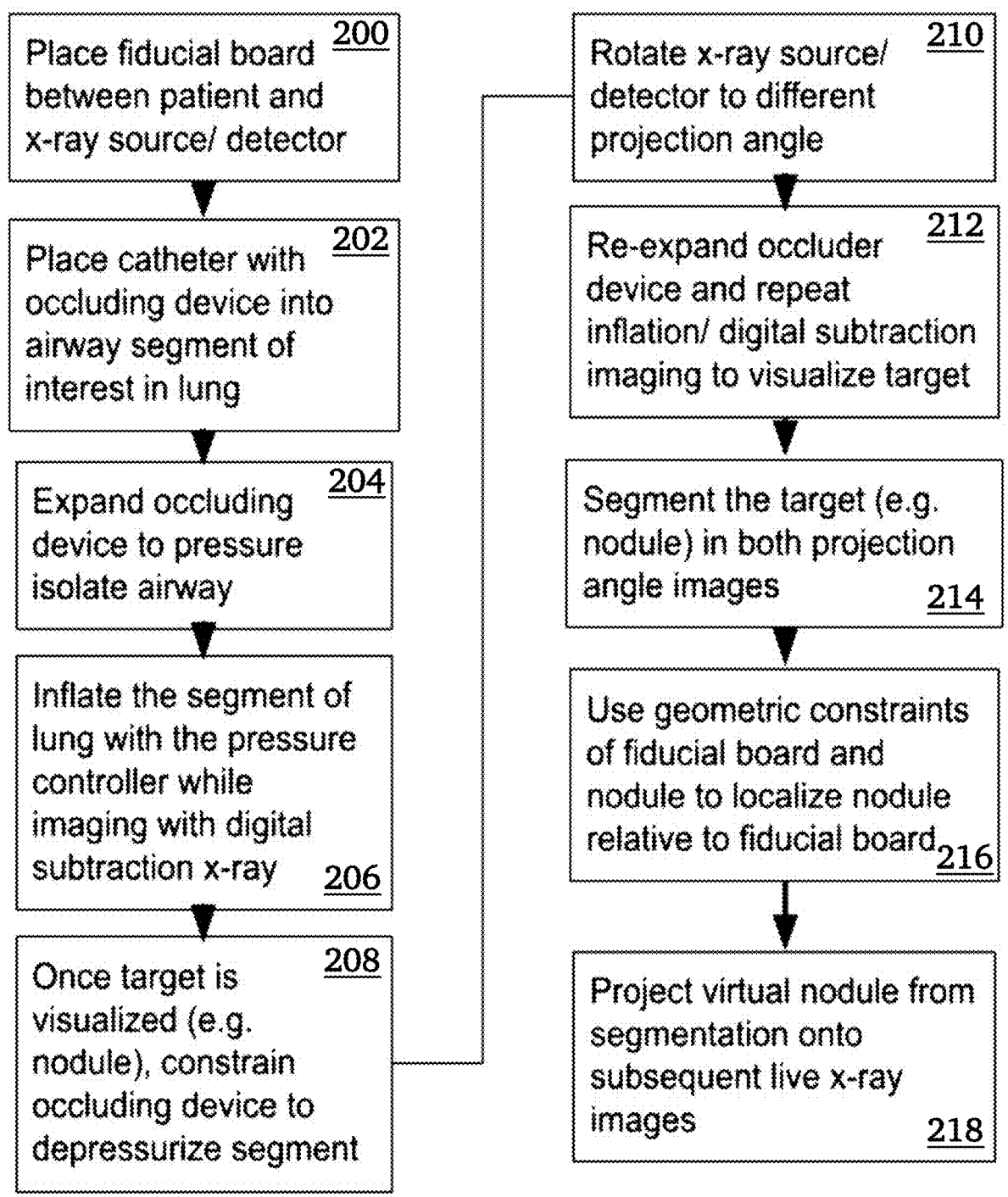
FIG. 2 is a flowchart illustrating a method to create virtual overlay of pulmonary structures onto live fluoroscopic images, according to an embodiment of the invention.

FIG. 2 is a flowchart illustrating a method according to one embodiment of the invention to create virtual overlay of pulmonary structures onto live fluoroscopic images. In step 200 a fiducial board is placed between a patient and the x-ray source/detector. In step 202 an occluding device such as a catheter with expandable balloon at its tip is placed into an airway containing a target of interest. In step 204, the occluding device is expanded to occlude the airway segment. In step 206, the segment of lung is inflated to a pressure in the range 1-100 cmH20 while imaging with digital subtraction until an image of the target (e.g. nodule) appears (series of images #1). In step 208, the balloon is deflated to allow the segment to depressurize. In step 210, the x-ray machine is rotated to a different angle (e.g. oblique or orthogonal) relative to the patient and fiducial marker board. In step 212, the balloon is expanded, the segment of lung is inflated with the controller device while imaging with digital subtraction until the target appears (series of images #2), and the balloon is deflated. In step 214, the nodule within both series of x-ray images (i.e. series #1 and #2) is located relative to the fiducial board and (manually or automatically via software) segmented. In step 216, the computer processor then localizes the nodule relative to the fiducial board using the geometric relationship between the segmented nodule in both locations relative to the fiducial marker beads. In step 218, the computer processor projects/overlays a virtual nodule onto subsequent live x-ray images collected without digital subtraction or inflation/deflation of the occluding device.

Key steps in the method include performing the air inflation procedure at two different x-ray projection angles, segmenting the nodule, and then using the known geometric constraints between the fiducial markers in the board and the segmented nodule in 2 different projection images to project a virtual image of the nodule onto subsequent live x-ray images. The location of the nodule can be determined from using the segmented nodule location in the two projection images combined with the known position of the beads in the fiducial marker board with known pose estimation algorithms (for example those published in "Visual Odometry" by Davide Scaramuzza in IEEE 2011). These steps differ from other virtual nodule fluoroscopic overlays (also termed augmented fluoroscopy) because in this description the spatial information of the nodule is derived solely from two series of fluoroscopic x-ray images taken at just two angles rather than from a previous CT reconstruction. Nodules are often invisible on fluoroscopic x-ray, but with air inflation and digital subtraction imaging the nodules can become visible. The fact that the nodule is visualized on subtraction fluoroscopic x-ray in two x-ray projection planes allows for precise localization of the nodule on subsequent projection images without is having to perform a CT reconstruction, saving the patient radiation and reducing procedure time. Further, because the nodule localization can be done during the procedure there is a higher degree of accuracy than if the nodule was segmented from a CT scan performed prior to the procedure.

Once the location of the nodule is known relative to the marker board, the nodule's location can also be used to update other navigation methods that are based on CT methods. For example, electromagnetic navigation and other augmented fluoroscopy methods that use the location of the nodule on previous CT to aid navigation can be improved by integrating the real-time location of the nodule taken from the air pressure images in two projection planes. Thus, the location of the nodule can be updated relatively quickly and with lower radiation doses than performing multiple angular rotations as is necessary when performing tomosynthesis or cone beam CT to locate and update the nodule location.

Once the nodule is located in two projection planes via air inflation, segmented either manually or automatically, and then projected onto live fluoroscopy x-ray images, then the virtual nodule location can be automatically adjusted for respiratory motion. This can be performed by automatically registering the location of high contrast objects in the inflation images with the corresponding location in the live images, and then adjusting the nodule location relative to these high contrast objects. For example, the inflation catheter location can be tracked on live fluoroscopic images, and if the catheter moves relative to the fiducial board markers, then the virtual nodule location can be corrected on the live images by a similar distance and direction. Alternatively, other high contrast structures can be used to adjust the location of the virtual nodule including the diaphragm which moves with respiration.

Because the virtual segmentation of the nodule was taken from two different projection angles, the nodule might appear to look different between the two angles. Thus, it might be beneficial to vary the appearance of the virtual nodule on the live projection images based on what projection angle the x-ray system is currently located. For example, if the nodule looks like a circle in the first set of subtraction images collected at projection angle 1 after subtraction imaging, but looks like a cylinder in the second set of subtraction images at projection angle 2, then the virtual overlay might show a cylinder in projection 2 and a circle in projection 1 on live images. Further, the appearance of the nodule between the two angles (which would not be explicitly known from the two sets of subtraction images) could be interpolated such that a continuously updated appearance of the virtual nodule on live projection images could be obtained, thus providing a better sense of 3-dimensionality.

Figure 3A:
FIGS. 3A-3E are images illustrating x-ray fluoroscopic images obtained during various steps of the method, according to an embodiment of the invention.
Figure 3B:
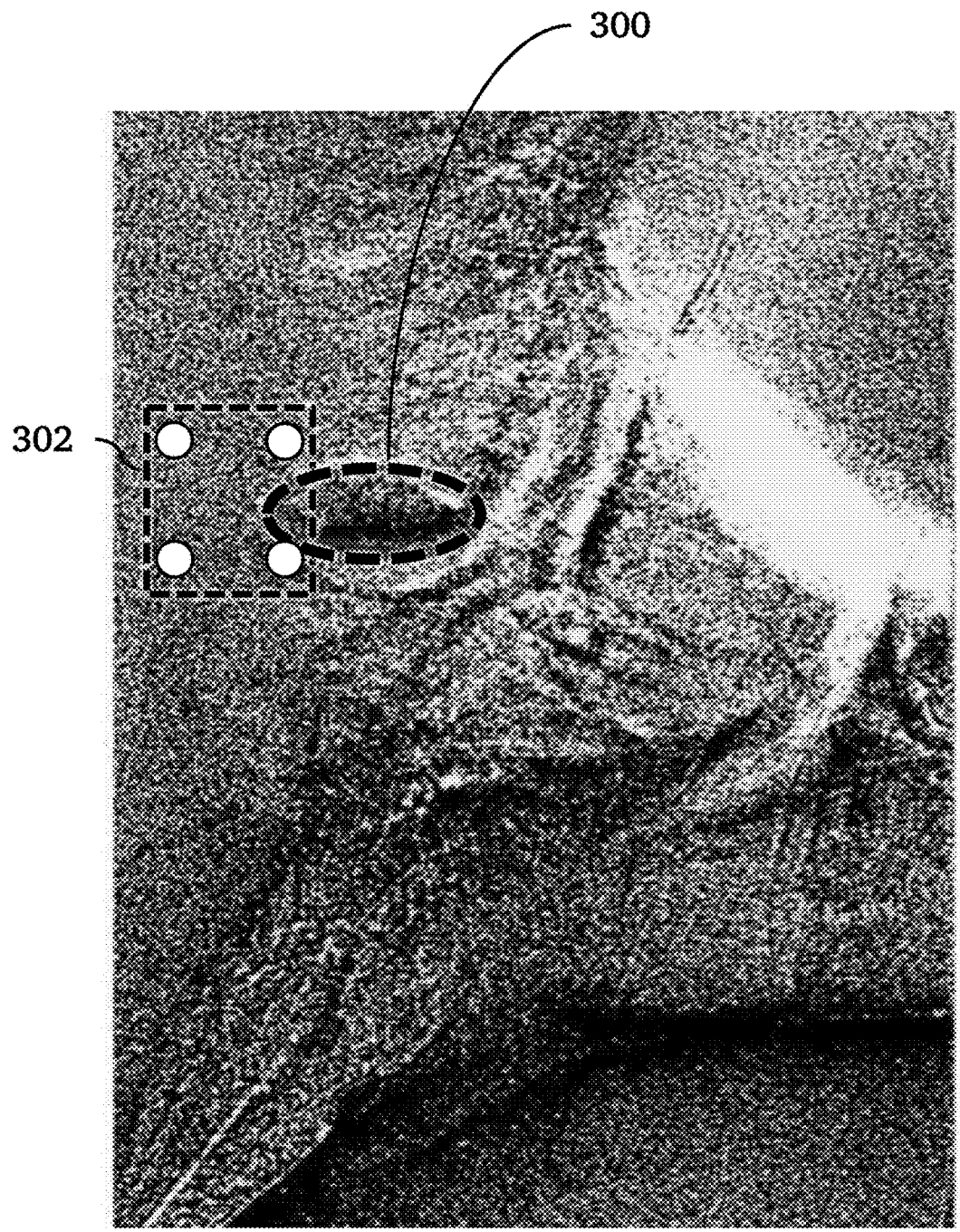
Figure 3C:
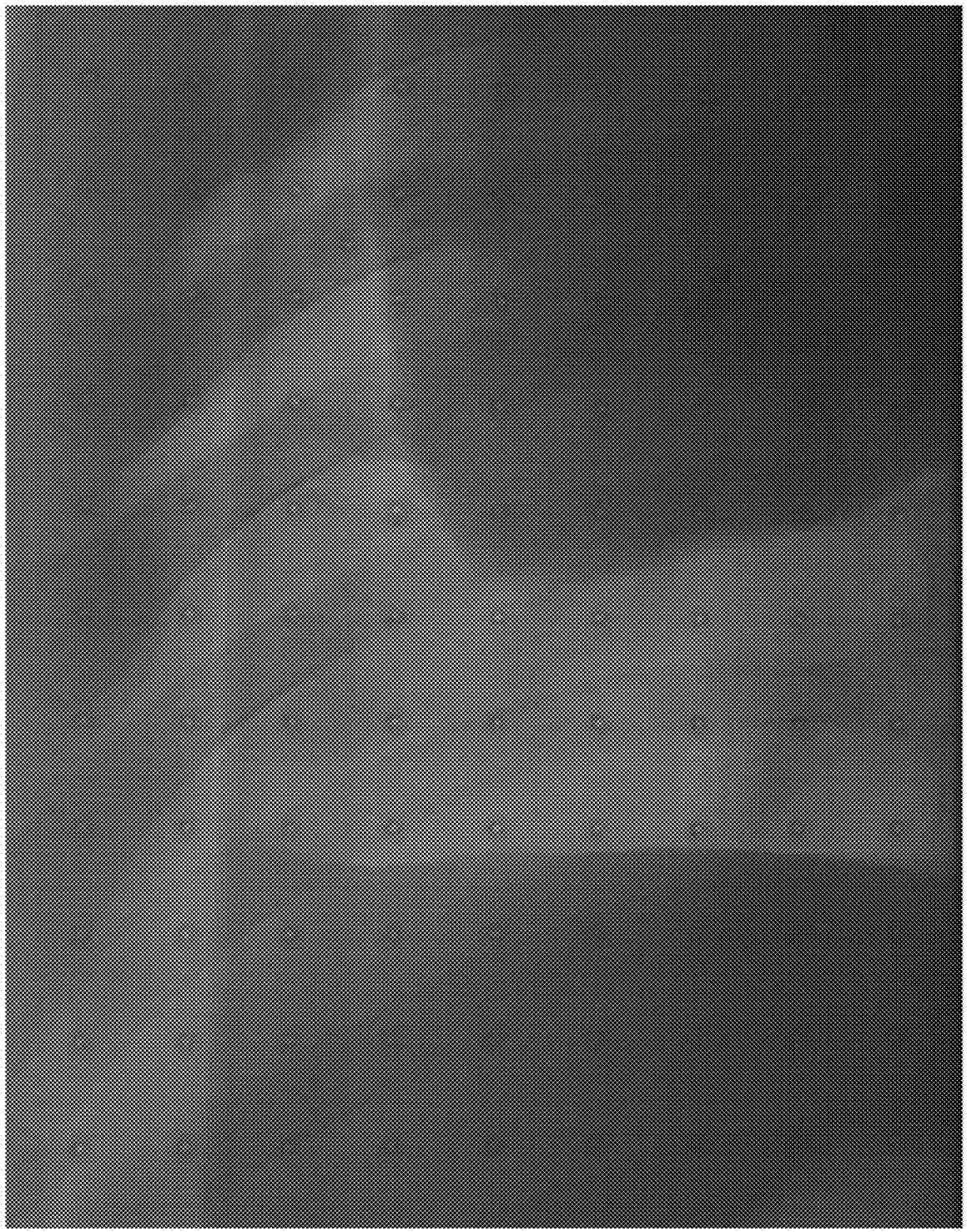
Figure 3D:
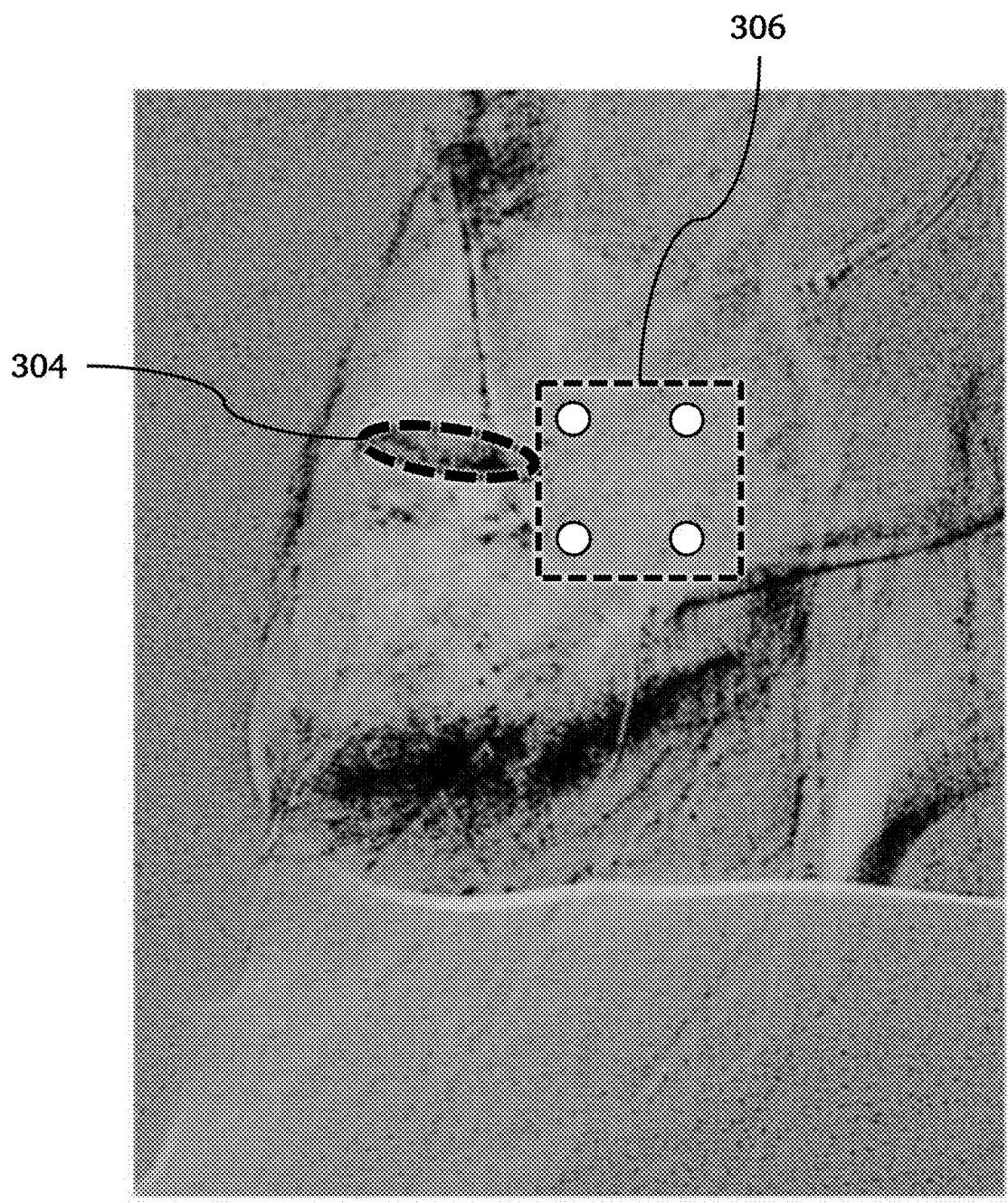
Figure 3E:
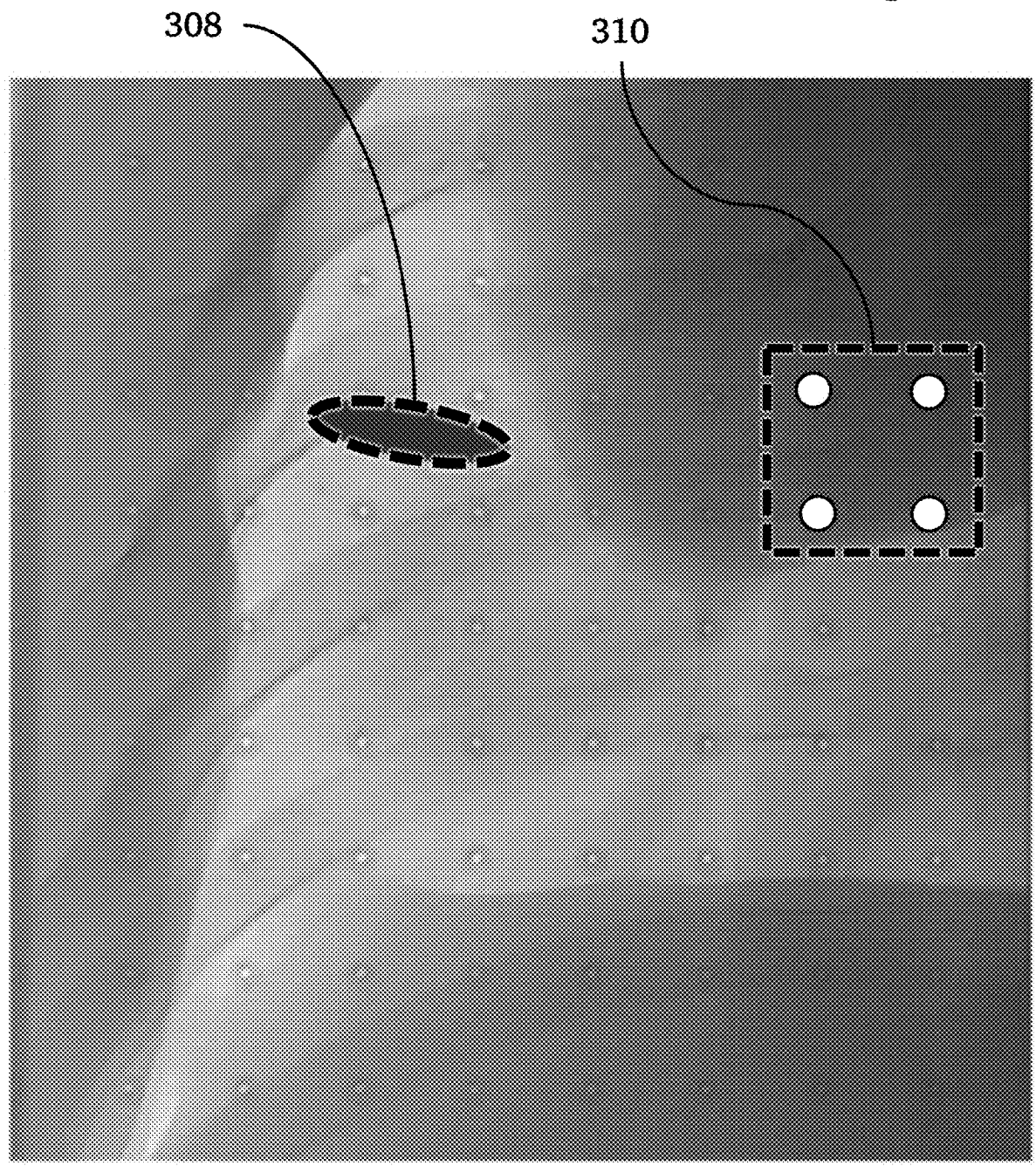

FIGS. 3A-E are images showing an example virtual overlay from a pig experiment. This series of images is an example of the virtual target overlay using images taken during a pig experiment. In this case, a pulmonary nodule was not readily visible on standard x-ray images (FIG. 3A). A balloon scope was inserted into the airway segment of interest and a balloon was inflated to occlude the segment. Air pressure was then imparted to the occluded segment while imaging with digital subtraction x-ray fluoroscopy. The nodule becomes visible as a black oblong region 300 (FIG. 3B). In this image, four fiducial markers 302 are shown. These specific markers remain highlighted throughout the series to show the fiducial board's relative position to the structures in the image as the x-ray system is rotated to additional positions. Once the nodule is visualized and segmented, the x-ray is rotated to another position where once again the nodule is not well visualized on x-ray (FIG. 3C). Additional images are then acquired with digital subtraction imaging and air inflation (FIG. 3D), which shows the nodule 304 and fiducial markers 306. The nodule is segmented/circled and the fiducial marker positions in the image have moved relative to the nodule location due to the change in the projection angle of the x-ray. Once the positions of the segmented nodule relative to the fiducial board in both projections has been determined, a virtual projection of the nodule can be overlaid on subsequent x-ray images where the nodule would otherwise have been invisible. Further, the x-ray system can be rotated to many different positions and the virtual nodule 308 will be displayed in the image with a position that will update based on the fiducial marker 310 positions (FIG. 3E), allowing for better 3D targeting of the nodule.

The invention claimed is:

1. A method of x-ray fluoroscopy comprising:
   imaging a region of interest at a first imaging projection angle using digital subtraction x-ray fluoroscopic imaging with a fiducial marker board positioned in a first field of view containing the region of interest to produce a first set of images;
   wherein the region of interest is a lung;
   wherein imaging the region of interest at the first imaging projection angle using digital subtraction x-ray fluoroscopic imaging comprises performing bronchoscopy with air pressure inflation of the lung near the pulmonary nodule during the digital subtraction x-ray fluoroscopic imaging;

imaging the region of interest at a second imaging projection angle using digital subtraction x-ray fluoroscopic imaging with the fiducial marker board positioned in a second field of view containing the region of interest to produce a second set of images;

wherein imaging the region of interest at the second imaging projection angle using digital subtraction x-ray fluoroscopic imaging comprises performing bronchoscopy with air pressure inflation of the lung near the pulmonary nodule during the digital subtraction x-ray fluoroscopic imaging:

determining image segmentation information to identify an anatomical feature in the region of interest imaged in the first set of images and the second set of images; wherein the anatomical feature is a pulmonary nodule;

imaging the region of interest using x-ray fluoroscopic imaging with the fiducial marker board positioned in a third field of view containing the region of interest to produce a third set of images;

projecting a virtual image of the anatomical feature onto the third set of images, where the virtual image is computed from the image segmentation information to identify the anatomical feature in the region of interest, from images of the fiducial marker board, and from a predetermined geometric relationship of markers within the fiducial marker board.

2. The method of claim 1
wherein performing bronchoscopy with air pressure inflation of the lung near the pulmonary nodule is performed using a catheter with an expandable occluding device disposed at a distal end, air pumps, and air valves.

3. The method of claim 1
wherein performing bronchoscopy with air pressure inflation of the lung near the pulmonary nodule comprises expanding an occluding device disposed at a distal end of a catheter to occlude an airway segment and inflating the airway segment.

4. The method of claim 1
wherein the fiducial marker board comprises multiple rows of radio-dense markers embedded within a board with a predetermined geometric arrangement.

5. The method of claim 1
wherein imaging the region of interest at the first imaging projection angle using digital subtraction x-ray fluoroscopic imaging is performed using a fluoroscopic x-ray C-arm device;

wherein imaging the region of interest at the second imaging projection angle using digital subtraction x-ray fluoroscopic imaging is performed using the fluoroscopic x-ray C-arm device; and wherein the method further comprises rotating the fluoroscopic x-ray C-arm device between imaging the region of interest at the first imaging projection angle and imaging the region of interest at the second imaging projection angle.

6. The method of claim 1
wherein determining the image segmentation information is performed automatically using digital image processing.

* * * * *